(12) United States Patent
Valli et al.

(10) Patent No.: US 7,473,540 B2
(45) Date of Patent: Jan. 6, 2009

(54) METHODS FOR SELECTING A YEAST POPULATION FOR THE PRODUCTION OF AN ORGANIC ACID AND PRODUCING AN ORGANIC ACID

(75) Inventors: Minoska Valli, Vienna (AT); Michael Sauer, Vienna (AT); Danilo Porro, Erba (IT); Paola Branduardi, Milan (IT); Diethard Mattanovich, Vienan (AT)

(73) Assignee: Tate & Lyle Ingredients Americas, Inc., Decatur, IL (US)

( * ) Notice: Subject to any disclaimer, the term of this patent is extended or adjusted under 35 U.S.C. 154(b) by 246 days.

(21) Appl. No.: 11/533,507

(22) Filed: Sep. 20, 2006

(65) Prior Publication Data

US 2007/0065899 A1    Mar. 22, 2007

Related U.S. Application Data

(60) Provisional application No. 60/720,968, filed on Sep. 27, 2005, provisional application No. 60/720,608, filed on Sep. 22, 2005.

(51) Int. Cl.
*C12P 7/56* (2006.01)
(52) U.S. Cl. .................................. 435/139; 435/41
(58) Field of Classification Search ................ 435/139, 435/41, 162
See application file for complete search history.

(56) References Cited

U.S. PATENT DOCUMENTS

| 2,024,565 A | 12/1935 | Braun ........................ 260/119 |
| 4,885,247 A | 12/1989 | Datta ......................... 435/139 |
| 4,954,450 A * | 9/1990 | Brothersen et al. ......... 435/252.4 |
| 5,068,418 A | 11/1991 | Kulprathipanja et al. .... 562/580 |
| 5,116,737 A * | 5/1992 | McCoy ........................ 435/42 |
| 5,464,760 A | 11/1995 | Tsai et al. .................... 435/139 |
| 5,503,750 A | 4/1996 | Russo, Jr. et al. ........... 210/641 |
| 5,510,526 A | 4/1996 | Baniel et al. ................. 562/580 |
| 5,574,180 A | 11/1996 | McQuigg et al. ............ 558/147 |
| 5,631,143 A | 5/1997 | Menart et al. .............. 435/69.1 |
| 5,641,406 A | 6/1997 | Sarhaddar et al. ........... 210/656 |
| 5,780,678 A | 7/1998 | Baniel et al. ................. 562/580 |
| 5,866,371 A | 2/1999 | Badziong et al. ........... 435/69.2 |
| 5,892,109 A | 4/1999 | Baniel et al. ................. 562/580 |
| 5,959,144 A | 9/1999 | Baniel ........................ 562/580 |
| 6,001,255 A | 12/1999 | Eyal et al. .................... 210/638 |
| 6,043,072 A | 3/2000 | Croteau et al. .............. 435/193 |
| 6,087,532 A | 7/2000 | Baniel et al. ................. 562/580 |
| 6,160,173 A | 12/2000 | Eyal et al. .................... 562/589 |
| 6,187,951 B1 | 2/2001 | Baniel et al. ................. 562/580 |
| 6,229,046 B1 | 5/2001 | Eyal et al. .................... 562/589 |
| 6,268,189 B1 | 7/2001 | Skory ......................... 435/139 |
| 6,280,985 B1 | 8/2001 | Caboche et al. ............. 435/139 |
| 6,319,382 B1 | 11/2001 | Norddahl .................... 204/530 |
| 6,320,077 B1 | 11/2001 | Eyal et al. .................... 562/589 |
| 6,429,006 B1 * | 8/2002 | Porro et al. ............... 435/254.2 |
| 6,475,759 B1 | 11/2002 | Carlson et al. .............. 435/139 |
| 6,485,947 B1 | 11/2002 | Rajgarhia et al. ........... 435/139 |
| 6,489,508 B1 | 12/2002 | Van Gansbeghe et al. ... 562/589 |
| 6,534,679 B2 | 3/2003 | Eyal et al. .................... 562/589 |
| 7,049,108 B2 * | 5/2006 | Porro et al. ................. 435/139 |
| 7,109,010 B2 | 9/2006 | Rajgarhia et al. ........... 435/190 |
| 2003/0129715 A1 | 7/2003 | Carlson et al. .............. 435/139 |
| 2003/0190630 A1 | 10/2003 | Rajgarhia et al. .............. 435/6 |
| 2003/0228671 A1 | 12/2003 | Hause et al. ................ 435/161 |
| 2004/0029238 A1 | 2/2004 | Rajgarhia et al. ........... 435/139 |
| 2004/0029256 A1 | 2/2004 | Rajgarhia et al. ........ 435/254.2 |
| 2005/0059136 A1 | 3/2005 | van Maris et al. ...... 435/254.21 |
| 2005/0112737 A1 | 5/2005 | Liu et al. ..................... 435/139 |

FOREIGN PATENT DOCUMENTS

| EP | 0 932 593 | 4/2002 |
| WO | WO94/00554 | 1/1994 |
| WO | WO94/01569 | 1/1994 |

(Continued)

OTHER PUBLICATIONS van Maris A. et al. Homofermentative Lactate Production Cannot Sustain Anaerobic Growth . . . Applied and Environmental Microbiology 70(5)2898-2905, May 2004.*

(Continued)

*Primary Examiner*—Ralph Gitomer
(74) *Attorney, Agent, or Firm*—Williams, Morgan & Amerson, P.C.

(57) ABSTRACT

A method of producing an organic acid by staining a yeast population with a stain capable of internal pH ($pH_i$)-dependent fluorescence, to yield a stained yeast population; determining a gate pH and a corresponding fluorescence parameter of the stained yeast population; and sorting the cells of the stained yeast population such that the cells having a $pH_i$ above the gate pH are retained and the cells having a $pH_i$ below the gate pH are discarded, to yield a yeast population for the production of the organic acid. Also, a method of producing an organic acid by performing the above steps, followed by isolating individual cells of the yeast population, to yield individual yeast cells for the production of an organic acid; culturing an individual yeast cell, to yield a cloned yeast population for the production of an organic acid; and incubating the cloned yeast population for the production of an organic acid in a medium containing an organic acid precursor, to produce the organic acid.

15 Claims, 9 Drawing Sheets

FOREIGN PATENT DOCUMENTS

| | | |
|---|---|---|
| WO | WO95/00660 | 1/1995 |
| WO | WO98/15518 | 4/1998 |
| WO | WO99/14335 | 3/1999 |
| WO | WO99/19503 | 4/1999 |
| WO | WO00/71738 | 11/2000 |
| WO | WO01/25180 | 4/2001 |
| WO | WO02/42471 | 5/2002 |
| WO | WO03/018480 | 3/2003 |
| WO | WO03/049525 | 6/2003 |
| WO | WO03/076616 | 9/2003 |
| WO | WO03/076630 | 9/2003 |
| WO | WO03/095659 | 11/2003 |
| WO | WO03/102152 | 12/2003 |
| WO | WO03/102200 | 12/2003 |
| WO | WO03/102201 | 12/2003 |
| WO | WO2004/014889 | 2/2004 |
| WO | WO2004/063382 | 7/2004 |
| WO | WO2004/099381 | 11/2004 |
| WO | WO2004/104202 | 12/2004 |
| WO | WO2005/033324 | 4/2005 |
| WO | WO2005/052174 | 6/2005 |
| WO | WO2005/071061 | 8/2005 |
| WO | WO2005/100543 | 10/2005 |
| WO | WO2005/123647 | 12/2005 |

OTHER PUBLICATIONS

Porro D. et al. Development of Metabolically Engineered *Saccharomyces cerevisiae* Cells for the Production of Lactic Acid. Biotechnology Prog 11, 294-298, 1995.*
Valli M. et al. Improvement of Lactic Acid Production in *S. cerevisiae* by Cell Sorting for High Intracellular pH. Applied and Environmental Microbiology 72(8)5492-5499, Aug. 2006.*
Sauer M. et al. Metabolic Engineering of Yeast. Recent Research Development Biotech & Bioengineering 4(2001)51-59.*
Narendranath N. et al. Acetic Acid and Lactic Acid Inhibition of Growth of *S. cerevisiae* by Different Mechanisms. J of the American Siciety of Brewing Chemists 59(4)187-194, 2001.*
Kreger-van Rij, *The Yeasts*, vol. 1, Chapter 2, pp. 5-61 (1987).
van Maris et al., *Appl. Env. Microbiol.* 70:2898-2905 (May 2004).
NCBI GenBank Accession No. AJ293008 (Aug. 3, 2004).
NCBI GenBank Accession No. M76708 (May 23, 2001).
NCBI GenBank Accession No. M22305 (May 23, 2001).
NCBI GenBank Accession No. M19396 (May 23, 2001).
NCBI GenBank Accession No. AF023920 (May 23, 2001).
NCBI GenBank Accession No. U24155 (May 30, 2001).
Zeeman et al., *Microbiology* 144(12):3437-3446 (1998).
Zülli et al., *Biol. Chem., Hoppe-Seyler* 368:1167-1177 (Sep. 1987).
Waldvogel et al., *Biol. Chem., Hoppe-Seyler* 368:1391-1399 (Oct. 1987).
Kim et al., *Appl. Environ. Microbiol.* 57:2413-2417 (Aug. 1991).
Stewart, *Biotechnology and Genetic Engineering Reviews* 14:67-143 (Apr. 1997).
Gena et al., *Microbiologica* 6(1):1-8 (1983) (Abstract).
Goffin et al., "Lactate Dehydrogenase-Independent Lactic Acid Racemization in *Lactobacillus Plantarum*" (2000).
Skory, *J. Ind. Microbiol. Biotechnol.* 30(1):22-27 (2003).
Skory, *App. Env. Microbiol.* 66(6):2343-2348 (Jun. 2000).
Porro et al., *Biotechnology Progress* 11:294-298 (1995).
Porro et al., *Res. Microbiology* 142:535-539 (1991).
Porro et al., *App. Env. Microbiol.* 65(9):4211-4215 (Sep. 1999).
"Production of Pyruvic Acid by Fermentation—Comprises Culturing Mutant of Torulopsis with Reduced Pyruvate Decarboxylase Activity," Derwent Publications Ltd., Abstract No. 88-348694 (Oct. 26, 1988).
Davis et al., *Proceedings of the National Academy of Sciences of USA* 89:11169-11173 (Dec. 1992).
Buckholz et al., *Biotechnology* 9:1067-1072 (Nov. 1991).
Hohmann, *Journal of Bacteriology* 173:7963-7969 (Dec. 1991).
Hohmann, *Yeast Sugar Metabolism* 11:187-211 (1997).
Witte et al., *J. Basic Microbiol.* 29:707-716 (1989).
Bianchi et al., *Molecular Microbiology* 19:27-36 (1996).
Bianchi et al., *App. Env. Microbiol.* 67(12):5621-5625 (Dec. 2001).
Chelstowska et al., *Yeast* 15(13):1377-1391 (1999).
Garvie, *Microbiological Reviews* 44(1):106-139 (Mar. 1980).
Lodi et al., *Mol. Gen. Genet.* 238:315-324 (1993).
Pallotta et al., *Biochimica et Biophysica Acta* 1608:104-113 (2004).
Adachi et al., *J. of Fermentation and Bioengineering* 86(3):284-289 (1998).
Chang et al., *App. Env. Microbiol.* 65(4):1384-1389 (Apr. 1999).
Zhou et al., *Applied Environ. Microbiol.* 69(1):399-407 (Jan. 2003).
Flikweert et al., *Yeast* 12:247-257 (1996).
Valli et al., *Applied and Environmental Microbiology* 71(3):1515-1521 (Mar. 2005).
Valli et al., *Applied and Environmental Microbiology* 72(8):5492-5499 (Aug. 2006).
Winson et al., *Methods* 21:231-240 (2000).
Ishida et al., *Applied and Environmental Microbiology* 71(4):1964-1970 (Apr. 2005).
Saitoh et al., *Applied and Environmental Microbiology* 71(5):2789-2792 (May 2005).

* cited by examiner

US 7,473,540 B2

METHODS FOR SELECTING A YEAST POPULATION FOR THE PRODUCTION OF AN ORGANIC ACID AND PRODUCING AN ORGANIC ACID

This application claims priority from U.S. provisional patent application Ser. No. 60/720,608, filed on Sep. 22, 2005, and U.S. provisional patent application Ser. No. 60/720,968, filed on Sep. 27, 2005, both of which are incorporated herein by reference.

BACKGROUND OF THE INVENTION

The present invention relates generally to the industrial use of microorganisms. More particularly, it concerns the production of organic acids in yeast.

Generally, an incubation medium having a low pH is favorable for the production of organic acids by yeast, as thereby the free acid is produced rather than the anionic form. However, the production of organic acids with microorganisms exerts a high stress on the cells: the culture medium is acidified, so that the microorganisms have to actively counteract the increased pH gradient across the plasma membrane. At low external pH ($pH_e$), organic acids exert additional stress on the cells, as they diffuse through the plasma membrane and acidify the cytoplasm. This effect adds to the general stress exerted by low pH. Yeasts counteract this acidification, and tend to maintain a near neutral intracellular pH ($pH_i$), but at some cost in viability and metabolic activity.

Given this stress, there is a limitation of productivity by using state of the art technology, as the yeast cells will eventually lose viability and metabolic activity. Therefore, there is interest in isolating more robust yeast strains, i.e., yeast strains capable of improved viability and metabolic activity at low pH. Any development that enables the isolation of more robust strains would be desirable for such production processes.

SUMMARY OF THE INVENTION

In one embodiment, the present invention relates to a method of producing an organic acid by staining a yeast population with a stain capable of internal pH ($pH_i$)-dependent fluorescence, to yield a stained yeast population; determining a gate pH and a corresponding fluorescence parameter of the stained yeast population; and sorting the cells of the stained yeast population such that the cells having a $pH_i$ above the gate pH are retained and the cells having a $pH_i$ below the gate pH are discarded, to yield a yeast population for the production of the organic acid.

In another embodiment, the present invention relates to a method of producing an organic acid by performing the above steps, followed by incubating the yeast population for the production of an organic acid in a medium containing an organic acid precursor, to produce the organic acid.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 2A a subpopulation of cells with high $pH_i$ (high slope of the cloud) and a subpopulation of cells with low $pH_i$ (low slope of the cloud) can be seen. FIG. 2B shows that the cells with low $pH_i$ are dead.

DESCRIPTION OF ILLUSTRATIVE EMBODIMENTS

Figure 1:
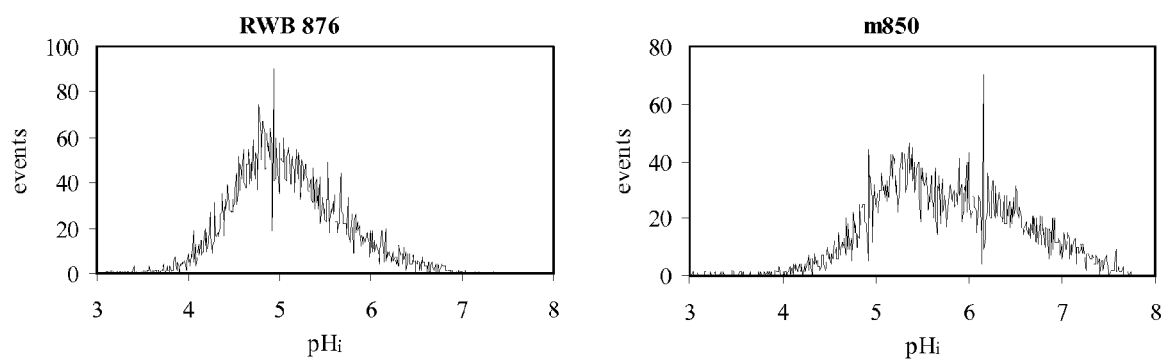
FIG. 1 shows histograms of the distribution of the $pH_i$ values in a cell population of the respective strains after 70 hours of growth for S. cerevisiae strains RWB 876 and m850.

In one embodiment, the present invention relates to the improved production of organic acids with yeasts at low pH. "Organic acid" is used herein to refer to any molecule comprising one or more —COOH moieties and at least one other carbon atom. In one embodiment, the organic acid has one, two, or three —COOH moieties and 3-8 carbon atoms. In one embodiment, the organic acid is selected from the group consisting of lactic acid, citric acid, malic acid, maleic acid, fumaric acid, adipic acid, succinic acid, tartaric acid, α-ketoglutaric acid, pyruvic acid, and oxaloacetic acid. In one embodiment, the organic acid is lactic acid.

We have analyzed the $pH_i$ of different yeast strains under conditions of lactic acid production, and discovered that strains showing better lactic acid production generally have higher $pH_i$. In light of this discovery, we have designed a method for isolating such yeast strains to yield a population of yeast suitable for the production of organic acids. In one embodiment, the method comprises fluorescence activated cell sorting (FACS) for the selection of robust strains with high lactic acid production.

In one embodiment, the present invention relates to a method of selecting a yeast population for the production of an organic acid, comprising:

staining a yeast population with a stain capable of internal pH ($pH_i$)-dependent fluorescence, to yield a stained yeast population;

determining a gate pH and a corresponding fluorescence parameter of the stained yeast population; and sorting the cells of the stained yeast population such that the cells having a $pH_i$ above the gate pH are retained and the cells having a $pH_i$ below the gate pH are discarded, to yield the yeast population for the production of the organic acid.

Typically yeast populations are heterogenous with respect to parameters like $pH_i$. This heterogeneity can be caused by genetic diversity. To increase diversity, the starting population of yeast can be mutagenized by any appropriate technique, such as the application of electromagnetic radiation (such as ultraviolet light (UV), gamma radiation, X-rays, or other) or a mutagenic compound (such as 5-bromouracil, 2-aminopurine, nitrous acid, hydroxylamine, N-methyl-N'-nitro-N-nitrosoguanidine, nitrogen mustards, mitomycin, or others) to the starting population of yeast. Any yeast known in the art for use in industrial processes can be used in the method as a matter of routine experimentation by the skilled artisan having the benefit of the present disclosure. The yeast to be transformed can be selected from any known genus and species of yeast. Yeasts are described by N. J. W. Kreger-van Rij, "The Yeasts," Vol. 1 of Biology of Yeasts, Ch. 2, A. H. Rose and J. S. Harrison, Eds. Academic Press, London, 1987. In one embodiment, the yeast genus can be *Saccharomyces, Zygosaccharomyces, Candida, Hansenula, Kluyveromyces, Debaromyces, Nadsonia, Lipomyces, Torulopsis, Kloeckera, Pichia, Schizosaccharomyces, Trigonopsis, Brettanomyces, Cryptococcus, Trichosporon, Aureobasidium, Lipomyces, Phaffia, Rhodotorula, Yarrowia,* or *Schwanniomyces,* among others. In a further embodiment, the yeast can be a *Saccharomyces, Zygosaccharomyces, Kluyveromyces* or *Pichia* spp. In yet a further embodiment, the yeasts can be *Saccharomyces cerevisiae. Saccharomyces cerevisiae* is a commonly used yeast in industrial processes, but the invention is not limited thereto.

Other techniques of compiling a population of yeast include exposing a starting yeast population to a selection agent or collecting a yeast population that is sufficiently large to be expected to contain a population arising from natural mutations, among others that will be apparent to the skilled artisan having the benefit of the present disclosure.

The yeast population can be stained with any stain capable of $pH_i$-dependent fluorescence. By "$pH_i$-dependent fluorescence" is meant that one or more of the intensity, wavelength, or other measurable parameters of the fluorescence of the stain is correlated with the $pH_i$ of the stained yeast. An exemplary stain is SNARF-4F 5-(and-6)-carboxylic acid, acetoxymethyl ester, acetate (cSNARF-4F). This compound belongs to the seminaphthorhodafluors stain family.

The stained yeast can be subjected to any sorting technique capable of sorting individual cells. In one embodiment, the sorting technique comprises fluorescence activated cell sorting (FACS). When sorting cells by FACS, it is necessary to define a gate that contains the wanted cells, but avoids the unwanted cells. Based on our observation described above, the skilled artisan having the benefit of the present disclosure can define a gate containing the cells having a high $pH_i$ of a value that can be determined as a matter of routine experimentation. The gate can be determined on absolute terms (cells having a fluorescence value correlated with a particular $pH_i$) or on relative terms (cells having a particular percentile rank of the $pH_i$ (determined by the fluorescence) value over the entire population). For example, the gate can be determined so that the cells having the 50% (or less) percentile rank of the $pH_i$ over the entire population, or the gate can be determined so that it contains the cells having the 10% (or less) percentile rank of the $pH_i$ over the entire population, or the gate can be determined so that it contains the cells having the 5% (or less) percentile rank of the $pH_i$ over the entire population, or the gate can be determined so that it contains the cells having the 2% (or less) percentile rank of the pHi over the entire population.

In another embodiment the gate pH can be determined to be 5.0 or higher, 6.0 or higher, or 7.0 or higher.

For example, when cSNARF-4F is the stain, cSNARF-4F shows pH-dependent emission spectra and in particular two inversely related emission signals at two different wavelengths ($\lambda 1=585$ nm and $\lambda 2=670$ nm). The pH of the cells can be calculated from the ratio between the fluorescence intensities measured at the two wavelengths through an appropriate calibration system. Based on the principle that the ratio of the fluorescence intensities ($\lambda 1$ divided by $\lambda 2$) is inversely correlated to the $pH_i$ of the cells, the slope (when plotted) of the cloud of cells is directly correlated to the $pH_i$. It is thus easy to identify in a dotplot the presence of two distinct subpopulations, one with high and one with low $pH_i$ (FIG. 2A).

After sorting, yeast cells having a $pH_i$ above the gate value are retained and yeast cells having a $pH_i$ below the gate value are discarded. Some amount of false positives (low $pH_i$ yeast retained after the sorting step) and false negatives (high $pH_i$ yeast discarded after the sorting step) may occur. To minimize the number of false positives, the sorting step can be repeated on the retained population multiple times, such as two, three, or four times, among others. To increase the number of cells, a cultivation step can be included between the sorting steps.

Another possible source of false positives can be nonviable cells. Therefore, in one embodiment, the method further comprises gating of viable cells such that living cells are retained and dead cells are discarded, to yield the yeast population for the production of the organic acid. In one embodiment, the gating can comprise the determination of an additional gate based on the ratio of forward scatter (FSC), which is related to cell size, to side scatter (SSC), which is related to the internal complexity of the cells (FIG. 4A). Generally speaking, a lower ratio for a particular yeast cell correlates to a lower cell volume and a greater likelihood of the cell being dead. In one embodiment, the gate comprising the viable cells can be used simultaneously with the gate pH for sorting (i.e., the sorting step can be performed in a manner such that only cells meeting both the $pH_i$ gate threshold and the viability threshold are retained). The sorting step can be performed once or any greater number of times, such as two, three, or four times, among others. To increase the number of cells, a cultivation step can be included between the sorting steps.

By performing the method, strains with a higher organic acid productivity can be selected.

In another embodiment, the present invention relates to a method of producing an organic acid, comprising:

staining a yeast population with a stain capable of internal pH (pHi)-dependent fluorescence, to yield a stained yeast population;

determining a gate pH and a corresponding fluorescence parameter of the stained yeast population;

sorting the cells of the stained yeast population such that the cells having a pHi above the gate pH are retained and the cells having a pHi below the gate pH are discarded, to yield a yeast population for the production of the organic acid; and incubating the yeast population for the production of an organic acid in a medium containing an organic acid precursor, to produce the organic acid.

In one embodiment, the method can further comprise:
isolating individual cells of the yeast population, to yield individual yeast cells for the production of an organic acid; and culturing an individual yeast cell, to yield a cloned yeast population for the production of an organic acid, followed by incubating as discussed above.

The staining, determining, and sorting steps can be as described above. Isolating individual cells of the yeast population can be performed by any appropriate technique, such as plating a dilute solution of retained yeast cells on a solid medium capable of sustaining yeast growth. Culturing an individual yeast cell can then comprise allowing the plated isolated yeast cells to grow into colonies of cloned yeast cells, each colony consisting essentially of clones of the isolated cell. Cells, whether from a single colony or a heterogeneous culture, can then be incubated in an appropriate medium, such as a liquid medium capable of sustaining yeast growth, containing an organic acid precursor, to produce the organic acid. The organic acid precursor can be any compound which the skilled artisan having the benefit of the present disclosure will understand could be converted by metabolic processes of the yeast to the desired organic acid. In one embodiment, the organic acid precursor can be glucose.

By performing the method, improved production of an organic acid can be effected. For example, as will be discussed in more detail below, based on the S. cerevisiae strain RWB 876, about 80% of the strains selected according to the examples showed an improved production of lactic acid.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Initially, two lactic acid producing strains were analyzed: *Saccharomyces cerevisiae* CEN.PK RWB 876 ("RWB 876") and *S. cerevisiae* CEN.PK m850 ("m850"). These two strains are very different in respect of their ability to produce lactic acid. The strain m850 can consume approximately all the 70 g/L of glucose present in the medium and produce circa 60-65 g/L of lactic acid, while the strain RWB 876 can use only half of the glucose and, as a consequence, its lactic acid production is strongly impaired. Flow cytometric analysis showed that the strain m850 has a higher $pH_i$ than RWB 876. In fact, when the cells were harvested after 70 hours of growth in the fermentation medium $pH_i$ mean values of 5.8 and 5.1 were determined for the strains m850 and RWB 876, respectively. In FIG. 1 are reported the $pH_i$ distributions of the above mentioned samples. In the strain RWB 876 there is a homogeneous $pH_i$ distribution, while in the strain m850 two subpopulations are present. One of these subpopulations consists of cells with a high $pH_i$ (between pH 6 and pH 7). Similar $pH_i$ values are usually observed early in a fermentation.

Figure 2:
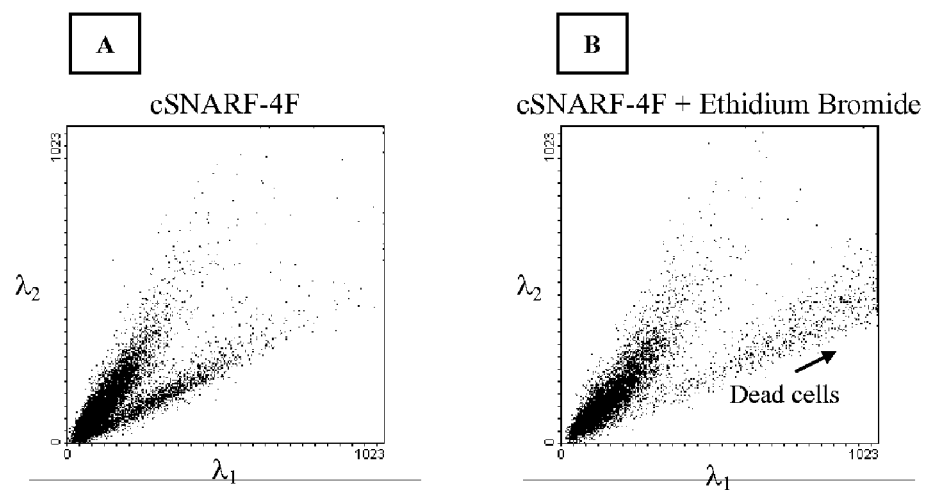
FIG. 2 shows a dotplot of the fluorescence emission of a sample of cells stained with the pH dependent probe (cSNARF-4F) (dotplot A) and a dotplot of the fluorescence emission of the same sample of cells stained simultaneously with cSNARF-4F and a viability probe (ethidium bromide) (dotplot B).

Furthermore, combined analysis of $pH_i$ and viability showed, in both strains, the appearance of a subpopulation of dead cells which are all characterized by low $pH_i$. FIG. 2 shows an example of this double staining. In these figures (dotplots) each dot represents one cell. For each cell, the value of one parameter is plotted against the value of a second parameter. Each dot therefore represents a pair of values for a single cell. In the first dotplot (FIG. 2A) is shown one sample of cells stained with a pH dependent probe (cSNARF-4F). This probe shows pH dependent emission spectra and in particular two inversely related emission signals at two different wavelengths ($\lambda 1=585$ nm and $\lambda 2=670$ nm). The pH of the cells can be calculated from the ratio between the fluorescence intensities measured at the two wavelengths through an appropriate calibration system. Based on the principle that the ratio of the fluorescence intensities ($\lambda 1$ divided by $\lambda 2$) is inversely correlated to the $pH_i$ of the cells, then the slope of the cloud of cells is directly correlated to the $pH_i$. It is thus easy to identify in the dotplot the presence of two distinct subpopulations, one with high and one with low $pH_i$ (FIG. 2A). In the second dotplot (FIG. 2B) the same sample of cells was simultaneously stained with cSNARF-4F and a viability probe (ethidium bromide). This probe can cross intact cytoplasmic membranes but is actively pumped out in healthy cells. Only impaired cells keep the ethidium bromide and show increased fluorescence emission. The comparison of FIGS. 2A-2B shows that during the double staining the subpopulation of cells with low $pH_i$ is also stained with ethidium bromide. Ethidium bromide fluorescence adds to cSNARF-4F fluorescence and increases the total fluorescence emission of the dead cells. As a consequence the dead cells shift to the right part of the dot plot. Two more viability probes were tested and confirmed that the cells belonging to the subpopulation with low $pH_i$ are dead.

Figure 3:
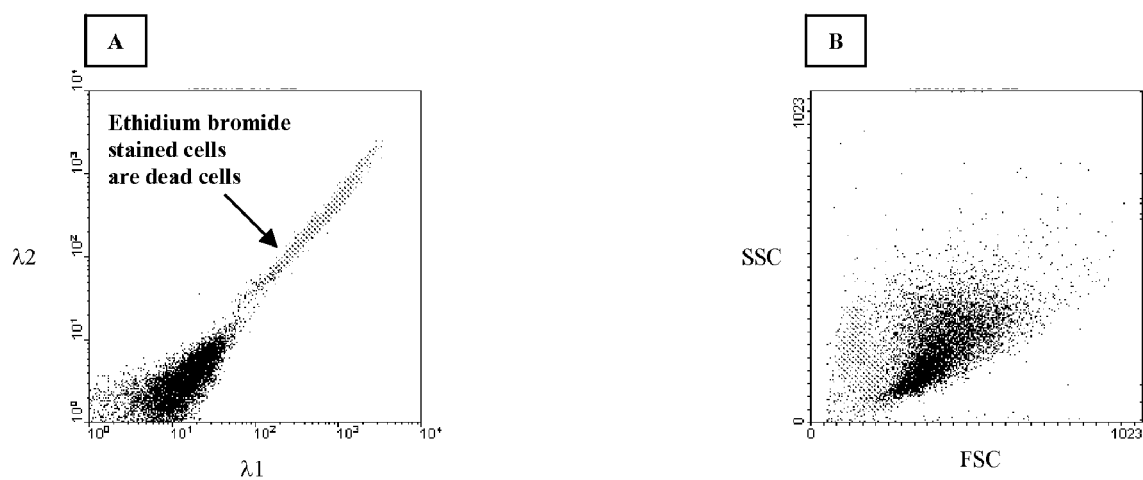
FIG. 3 shows a dotplot of the fluorescence emission of a sample of cells stained with a viability probe (ethidium bromide) (dotplot A) and a dotplot of the forward scatter (FSC) and side scatter (SSC) of the same sample of cells (dotplot B).

Furthermore, the analysis of ethidium bromide stained samples showed that the dead cells have reduced cell volume (FIG. 3). In FIG. 3A is reported the dotplot of a sample of cells stained only with ethidium bromide. On this plot the dead cells are shown in gray. We then analyzed two more parameters: the forward scatter (FSC), which is related to cell size, and the side scatter (SSC), which is related to the internal granularity or complexity of the cell. The dead cells defined with ethidium bromide remain marked in gray in this plot. Interestingly, we could observe that the dead cells (gray color) have all a smaller volume than the viable cells (FIG. 3B).

The results obtained analyzing the $pH_i$ and the viability of m850 and RWB 876 suggested the existence of a correlation between the ability of the cells to keep a high $pH_i$ and their ability to produce and tolerate high amount of lactic acid. Thus, with the hypothesis that cells with the highest $pH_i$ are the healthy cells, we designed an experiment aimed to the selection of cells which are better able to maintain the $pH_i$ during the production of lactic acid.

EXAMPLE 2

The strain RWB 876 was first subjected to UV mutagenesis (see Materials and Methods, below), and cultivated in liquid medium.

Figure 4:
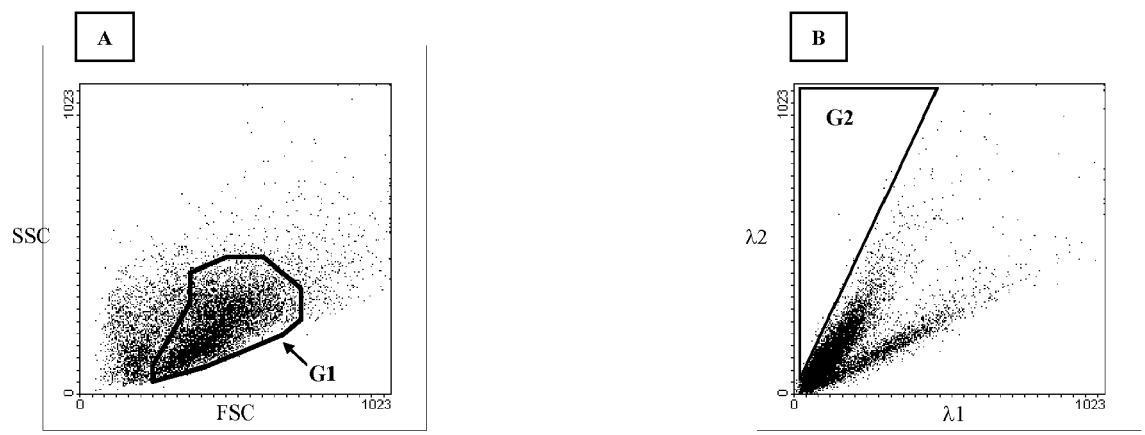
FIG. 4 shows a dotplot revealing how the gate which contained viable cells (gate G1) was designed (dotplot A) and a dotplot revealing how the gate which contains the cells with high $pH_i$ (gate G2) was designed (dotplot B).

After circa 65 hours of growth, samples of cells were stained with cSNARF-4F and analyzed by flow cytometry. We then proceeded with the definition of the gates for sorting. A gate was defined as an area on a dot plot which includes the desired cells (FIG. 4). According to the results previously described (FIGS. 3A and 3B), the gate G1 was designed on the dotplot FSC vs. SSC, which contains the viable cells (FIG. 4A). The gate G2 was defined on the dotplot $\lambda 1$ vs. $\lambda 2$ (FIG. 4B). Based on the principle of the $pH_i$ determination protocol (FIG. 2A), we selected for cells having a low ratio of fluorescence, thus a high $pH_i$. Notably, the gate G2 was defined in a way to include only a small percentage of cells (2-4%). Only the cells belonging to both gates were sorted and recovered. The sorting was performed in a sterile environment on approximately $5 \times 10^6$ cells of the UV mutagenized strain. The sorted cells were afterwards recovered in liquid medium. This procedure was repeated two times, so that a total of three consecutive rounds of sorting were performed. After the last round 5% of the cells were plated to allow the isolation of single presumptive mutants.

At every round of sorting of the UV mutagenized RWB 876 strain, we observed an increase in the percentage of cells belonging to both sorting gates, thus an increase of the percentage of cells with a high $pH_i$.

Figure 5:
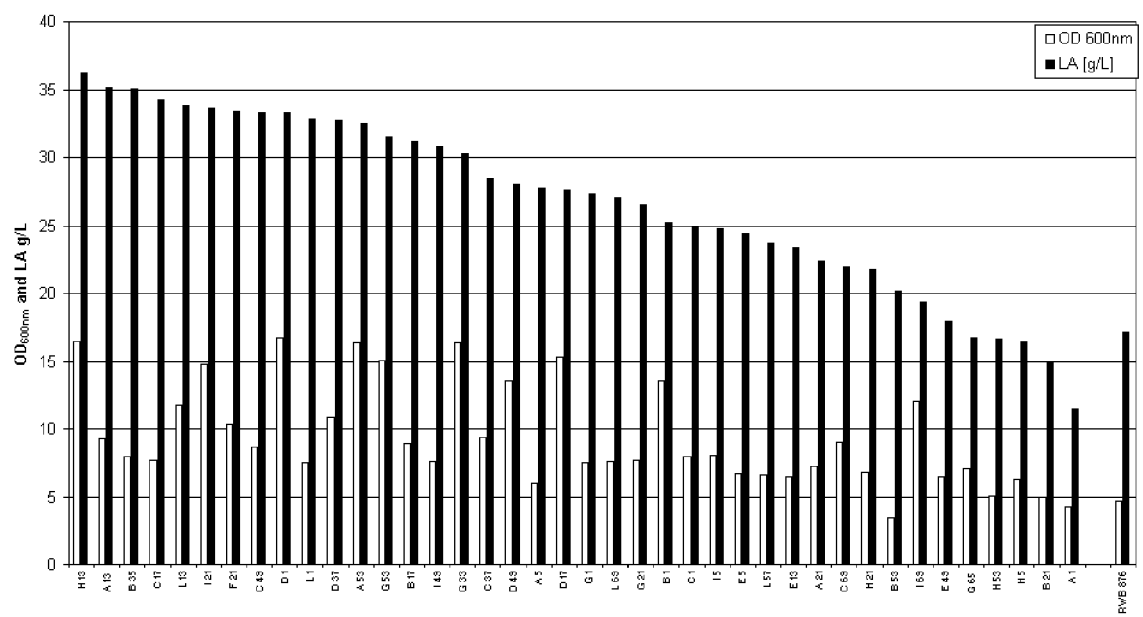
FIG. 5 shows a bar graph of the optical density ($OD_{600\ nm}$) and the lactic acid produced (LA g/L) after 70 hours of growth for 40 strains isolated from the UV mutagenized and sorted RWB 876 strain of Example 2, compared with the parental strain RWB 876 (right side of the plot).

We proceeded with the screening of presumptive mutants isolated from the UV mutagenized and sorted RWB 876 strain. The kinetics of lactic acid production were determined in the fermentation medium in parallel with the parental strain RWB 876 as a control. In FIG. 5 the results obtained with 40 presumptive mutants after 70 hours of growth are reported. The screening showed that 80% of the presumptive mutants had an improved lactic acid production compared to the parental strain RWB 876.

Materials and Methods

Strains

*S. cerevisiae* CEN.PK RWB 876 corresponds to the strain RWB 837YEpLpLDH (Pronk et al. (2004) Appl. Env. Microbiol 2898-2905).

Growth Conditions

Agar plates: 20 g/L agar, 1.7 g/L YNB, 5 g/L $(NH_4)_2SO_4$, 10 ml/L ethanol, 10 ml/L glycerol Preinoculum medium: 0.31 g/L $CaCO_3$, 1.7 g/L YNB, 1.5 g/L urea, 0.5 g/L glucose, 10 ml/L ethanol Fermentation medium: 4.5 g/L $CaCO_3$, 1.7 g/L YNB, 1 g/L urea, 70 g/L glucose, 5 ml/L ethanol 100 ml of medium in 250-ml quadruple baffled shake flask Incubation at 28° C.

UV Mutagenesis Protocol

All mutagenesis steps were performed in the dark. In order to prevent photoreactivation (repair of UV-induced DNA lesion in presence of light), cells just exposed to UV were also protected from the light. Mutagenized cells were kept in the dark for two-three days.

1) Determination of the UV Exposition Time

Several UV mutagenesis rounds were performed with the aim to determine for both strains the correct UV exposition time. This is, by definition, the time of UV exposure which allows only a small percentage of cells (between about 0.1% and 1%), to form a colony.

The cells were inoculated at initial optical density of $OD_{600}=3$ in the fermentation medium and harvested after 16 hours (RWB 876). The cells were washed once with sterile buffer (NaCl 0.9%), centrifuged 2 min at 13000 rpm and resuspended in 10 ml of sterile buffer in order to have $8 \times 10^6$ cells/ml as a final concentration. The cell suspension was then transferred in an empty sterile plate and exposed under the UV Lamp (253 nm) at a distance of 34 cm. The plate was opened and the UV lamp switched on. Samples of 100 µl were collected at fixed times of UV exposition (0', 2', 4', 5', 6', 7', 8' and 10') and added to 9.9 ml of sterile water in order to have a final concentration of $8 \times 10^4$ cells/ml. 1 ml of each of these suspensions, containing $8 \times 10^4$ cells, was plated by inclusion in minimal medium. The number of c.f.u was determined after 5 days of growth. For RWB 876 an optimum exposure time of 7.5 minutes was determined. After this exposure time only 0.5% of the cells were able to form a colony.

2) Protocol for UV Mutagenesis

The mutagenesis was performed on both strains on a total number of $8 \times 10^8$ cells. To do so, 10 plates each containing 10 ml of a cell suspension with $8 \times 10^6$ cells/ml were exposed to UV for the previously determined exposition time. The mutagenized cells were transferred in sterile tubes and collected by centrifugation (10 min at 3000 rpm). The cells were then recovered in liquid medium (medium for preinoculum) and after 5 days of growth used to inoculate the fermentation medium.

$pH_i$ Determination Protocol

Chemicals and Buffers

A stock solution of 5 mM carboxy SNARF-4F AM from Molecular Probes (SNARF-4F 5-(and-6)-carboxylic acid, acetoxymethyl ester, acetate) was prepared in DMSO. The stock solution of 9.7 mM amphotericin B from Sigma-Aldrich was obtained by dissolving 100 mg of the powder, which contains 45 mg of amphotericin B, in 5 ml of water. McIlvaine buffers were made by the combination of appropriate volumes of 100 mM citric acid and 200 mM $Na_2HPO_4$ to obtain a buffer of the desired pH. The loading buffer was prepared by dilution of the carboxy SNARF-4F AM stock solution in McIlvaine buffer of the pH 3.0 to a final concentration of 20 µM, stored on ice and protected from the light.

Cell Loading

For every measurement a cell sample corresponding to 1 ml at 0.25 $OD_{600}$ was collected by centrifugation with 13000 rpm for 2 min and resuspended in 250 µl of the loading buffer. After incubation at 28° C. for 11 min on a shaker, the cells were collected by centrifugation at 13000 rpm for 2 min and resuspended in 250 µl of McIlvaine buffer pH 3.0. The samples were put on ice and immediately analyzed by flow cytometry. For the overall experiments the samples were protected from the light, in order to guarantee the stability of the probe.

Flow Cytometric Analysis

Flow cytometric analyses were performed on a FACS Calibur (Becton Dickinson, Franklin Lakes, N.J., USA). The probe was excited with 15 mW 488 nm air-cooled argon-ion laser while the fluorescence emission was measured through a 585/21 bandpass filter ($\lambda 2$) and a 670 longpass filter ($\lambda 3$). All data were acquired in a linear mode. Threshold settings were adjusted so that the cell debris was excluded from the data acquisition. 10000 cells were measured for every sample. Data analysis was performed afterwards with the WinMDI 2.8 software. The ratio of fluorescence emission was calculated for every cell by dividing the emission signal at 585 nm by the emission signal at 670 nm. For any sample the mean $pH_i$ was calculated from the mean of the ratios of all cells, using the calibration described below.

In Situ Calibration

An in situ calibration was generated for each experiment. An appropriate quantity of cells was collected and, after loading with the protocol previously described, divided into different tubes (250 µl for each tube). The pellets were collected by centrifugation with 13000 rpm for 2 min and resuspended in 250 µl of McIlvaine buffers having different pH values. After the addition of amphotericin B to a final concentration of 30 µM the cells were incubated at 37° C. for 1 h on a shaker and then analyzed by flow cytometry. The calibration curve, constructed by plotting the fluorescence ratio of the different samples as a function of the pH of the buffer in which they were incubated, was fitted with a second-order polynomial function. The fitted data were used to generate an equation which converts fluorescence ratio to $pH_i$ values.

Viability Staining Protocol
Chemicals and Buffers
The loading buffer was made by diluting a stock solution of ethidium bromide in McIlvaine buffer at pH 3.0 to have a final concentration of 30 mg/L.

Cell Loading

For every measurement a cell sample corresponding to 1 ml at 0.25 $OD_{600}$ was collected by centrifugation with 13000 rpm for 2 min and resuspended in 250 µl of the loading buffer. After incubation at room temperature for 1 min the cells were collected by centrifugation at 13000 rpm for 2 min and resuspended in 250 µl of McIlvaine buffer pH 3.0. The samples were put on ice and immediately analyzed by flow cytometry.

Flow Cytometric Analysis

Flow cytometric analyses were performed on a FACS Calibur (Becton Dickinson, Franklin Lakes, N.J., USA). The probe was excited with 15 mW 488 nm air-cooled argon-ion laser while the fluorescence emission was measured through a 585/21 bandpass filter ($\lambda 2$) and a 670 longpass filter ($\lambda 3$). Threshold settings were adjusted so that the cell debris was excluded from the data acquisition. 10000 cells were measured for every sample.

The residual glucose and the lactic acid produced were determined with enzymatic kits from Megazyme.

EXAMPLE 3

Selection of Strain C49 from the Strain m850 Strain

*S. cerevisiae* CEN.PK m850 corresponds to the strain m850. This strain was selected from the strain CEN.PK RWB 876.

UV Mutagenesis Protocol

All the process of mutagenesis were performed as previously described for the strain RWB 876. The only differences in the protocol concern the time of growth of the cells before harvesting and the exposition time.

1) The cells were harvested for the mutagenesis step after 14 hours of growth.

2) The optimum exposition time for the strain m850 was 5 minutes.

Growth Conditions for UV Mutagenesis and Sorting Rounds

Agar plates: 20 g/L agar, 1.7 g/L YNB, 5 g/L $(NH_4)_2SO_4$, 10 ml/L ethanol, 10 ml/L glycerol Preinoculum medium: 0.31 g/L $CaCO_3$, 1.7 g/L YNB, 1.5 g/L urea, 0.5 g/L glucose, 10 ml/L ethanol Fermentation medium: 4.5 g/L $CaCO_3$, 1.7 g/L YNB, 1 g/L urea, 70 g/L glucose, 5 ml/L ethanol Preinoculum: cells were harvested from a fresh agar plate, inoculated at $OD_{600\,nm}$ 0.3 in 100 ml of preinoculum medium in a 250-ml quadruple baffled shake flask, and incubated at 28° C.

Inoculum: cells from the preinoculum were harvested after 24 hours of growth, inoculated at $OD_{600\,nm}$ 3.0 in 100 ml of fermentation medium in a 250-ml quadruple baffled shake flask, and incubated at 28° C.

Growth Conditions for Screening

Agar plates: 20 g/L agar, 1.7 g/L YNB, 5 g/L $(NH_4)_2SO_4$, 10 ml/L ethanol, 10 ml/L glycerol Preinoculum medium: 0.31 g/L $CaCO_3$, 1.7 g/L YNB, 1.5 g/L urea, 0.5 g/L glucose, 10 ml/L ethanol Fermentation medium: 4.5 g/L $CaCO_3$, 1.7 g/L YNB, 1 g/L urea, 70 g/L glucose, 5 ml/L ethanol Preinoculum: cells were harvested from a fresh agar plate, inoculated at $OD_{600\,nm}$ 0.3 in 20 ml of preinoculum medium in a 100-ml shake flask, and incubated at 28° C.

Inoculum: cells from the preinoculum were harvested after 40 hours of growth, inoculated at $OD_{600\,nm}$ 3.0 in 20 ml of fermentation medium in a 100-ml shake flask, and incubated at 28° C.

Figure 6:
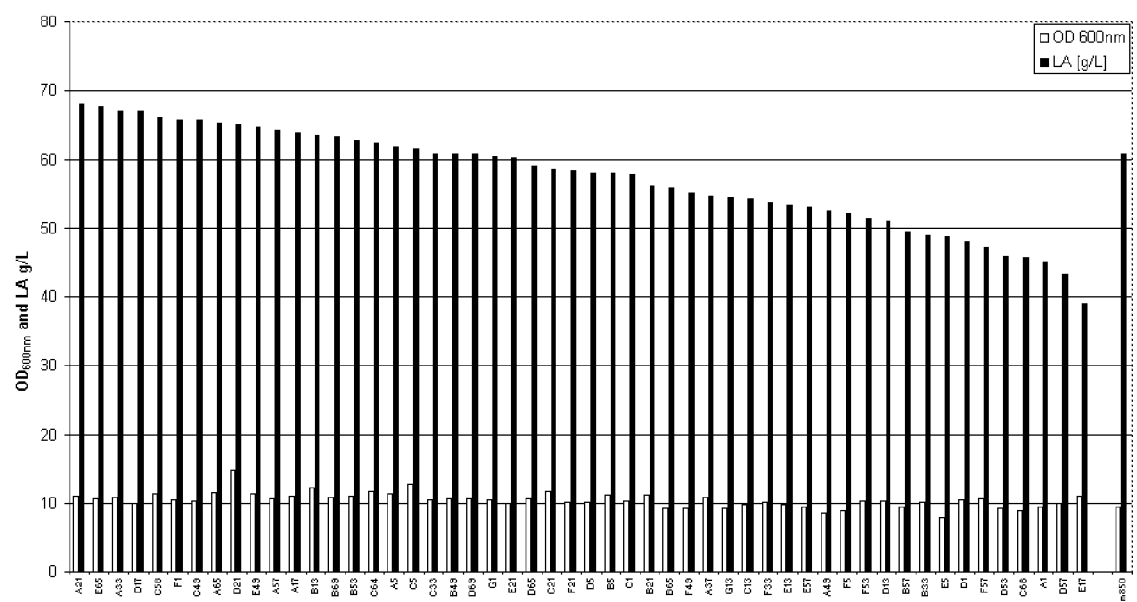
FIG. 6 shows a bar graph of the optical density ($OD_{600\ nm}$) and the lactic acid produced (LA g/L) after 70 hours of growth for 52 strains isolated from the UV mutagenized and sorted strain m850 of Example 3, compared with the parental strain m850 (right side of the plot).

FIG. 6 shows the results of screening of 52 presumptive mutants isolated from the UV mutagenized and sorted m850 strain. In the plot the optical density ($OD_{600\,nm}$) and the lactic acid produced (LA g/L) after 70 hours of growth are reported. The 52 presumptive mutants are compared with the parental strain m850 (right side of the plot).

EXAMPLE 4

Selection and Testing of Strains Z22 and Z26 from the Strain m850 and of Strain Y27 from Strain C49

Strains
CEN.PK m850
CEN.PK m850 strain C49 (selected from UV mutagenized and sorted (with 70 g/l glucose) m850 strain)

UV Mutagenesis Protocol

All the processes of mutagenesis were performed as previously described for the strain RWB 876 (Example 2). The only differences in the protocol concern the time of growth of the cells before harvesting and the exposure time.

1) For both strains the cells were harvested for the mutagenesis step after 14 hours of growth.

2) The optimum exposure time for strain m850 and strain C49 were 5 and 7 minutes, respectively.

Growth conditions for UV mutagenesis were as previously described for m850 and RWB 876.

Growth Conditions for Sorting

Agar plates: 20 g/L agar, 1.7 g/L YNB, 5 g/L $(NH_4)_2SO_4$, 10 ml/L ethanol, 10 ml/L glycerol Preinoculum medium: 0.31 g/L $CaCO_3$, 1.7 g/L YNB, 1.5 g/L urea, 0.5 g/L glucose, 10 ml/L ethanol Fermentation medium: 4.5 g/L $CaCO_3$, 1.7 g/L YNB, 1 g/L urea, 100 g/L glucose, 5 ml/L ethanol Preinoculum: cells were harvested from a fresh agar plate, inoculated at $OD_{600\,nm}$ 0.3 in 100 ml of preinoculum medium in a 250-ml quadruple baffled shake flask, and incubated at 28° C.

Inoculum: cells from the preinoculum were harvested after 24 hours of growth, inoculated at $OD_{600\,nm}$ 3.0 in 100 ml of fermentation medium in a 250-ml quadruple baffled shake flask, and incubated at 28° C.

Growth Conditions for Screening

Agar plates: 20 g/L agar, 1.7 g/L YNB, 5 g/L $(NH_4)_2SO_4$, 10 ml/L ethanol, 10 ml/L glycerol Preinoculum medium: 0.31 g/L $CaCO_3$, 1.7 g/L YNB, 1.5 g/L urea, 0.5 g/L glucose, 10 ml/L ethanol Fermentation medium: 4.5 g/L $CaCO_3$, 1.7 g/L YNB, 1 g/L urea, 100 g/L glucose, 5 ml/L ethanol Preinoculum: cells were harvested from a fresh agar plate, inoculated at $OD_{600\,nm}$ 0.3 in 20 ml of preinoculum medium in a 100-ml shake flask, and incubated at 28° C.

Inoculum: cells from the preinoculum were harvested after 40 hours of growth, inoculated at $OD_{600\,nm}$ 3.0 in 20 ml of fermentation medium in a 100-ml shake flask, and incubated at 28° C.

Growth Conditions for Analyses of the Selected Strains

Agar plates: 20 g/L agar, 1.7 g/L YNB, 5 g/L $(NH_4)_2SO_4$, 10 ml/L ethanol, 10 ml/L glycerol Preinoculum medium: 0.31 g/L $CaCO_3$, 1.7 g/L YNB, 1.5 g/L urea, 0.5 g/L glucose, 10 ml/L ethanol Fermentation medium: 2.78 g/L CaCO$_3$, 1.7 g/L YNB, 1 g/L urea, glucose concentration as reported in the different experiments (glucose concentration either 75, 80 and 90 g/L), 5 ml/L ethanol Preinoculum: cells were harvested from a fresh agar plate, inoculated at OD$_{600\,nm}$ 0.3 in 100 ml of preinoculum medium in a 250-ml triple baffled Bellco® flask, and incubated at 28° C.

Inoculum: cells from the preinoculum were harvested after 24 hours of growth, inoculated at OD$_{600\,nm}$ 3.0 in 100 ml of fermentation medium in a 250-ml triple baffled Bellco® flask, and incubated at 28° C.

Figure 7:
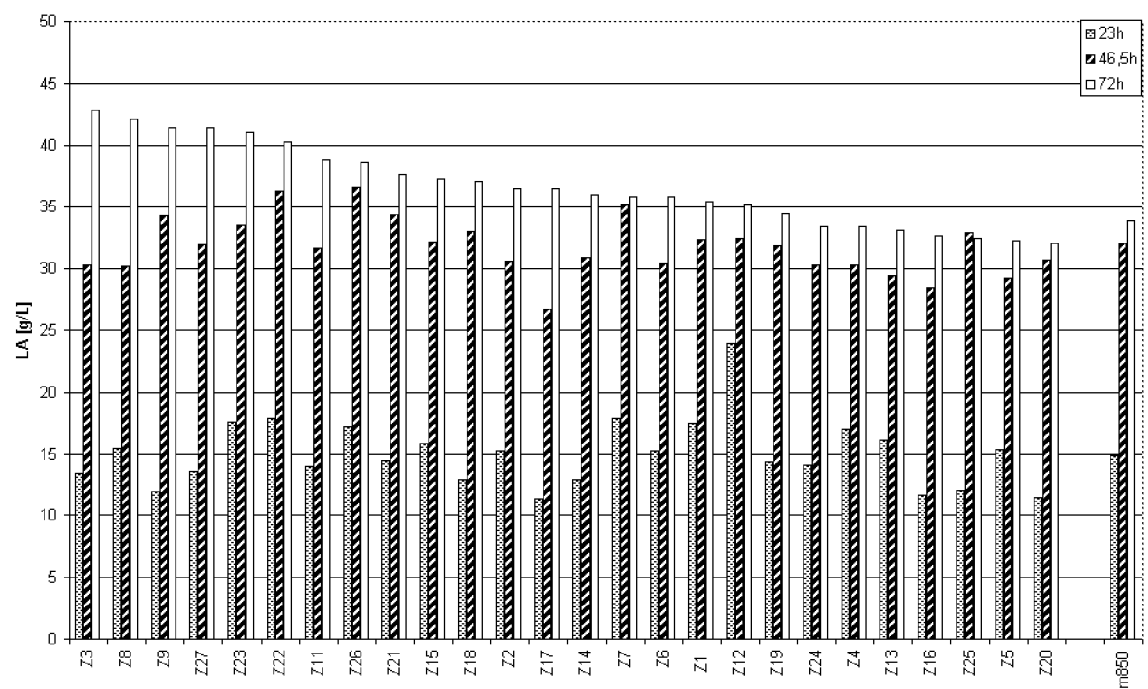
FIG. 7 shows a bar graph of the lactic acid produced (LA g/L) after 23, 46.5 and 70 hours of growth are reported for 26 strains derived from mutagenesis of m850 and compared with the parental strain m850 (right side of the plot).
Figure 8:
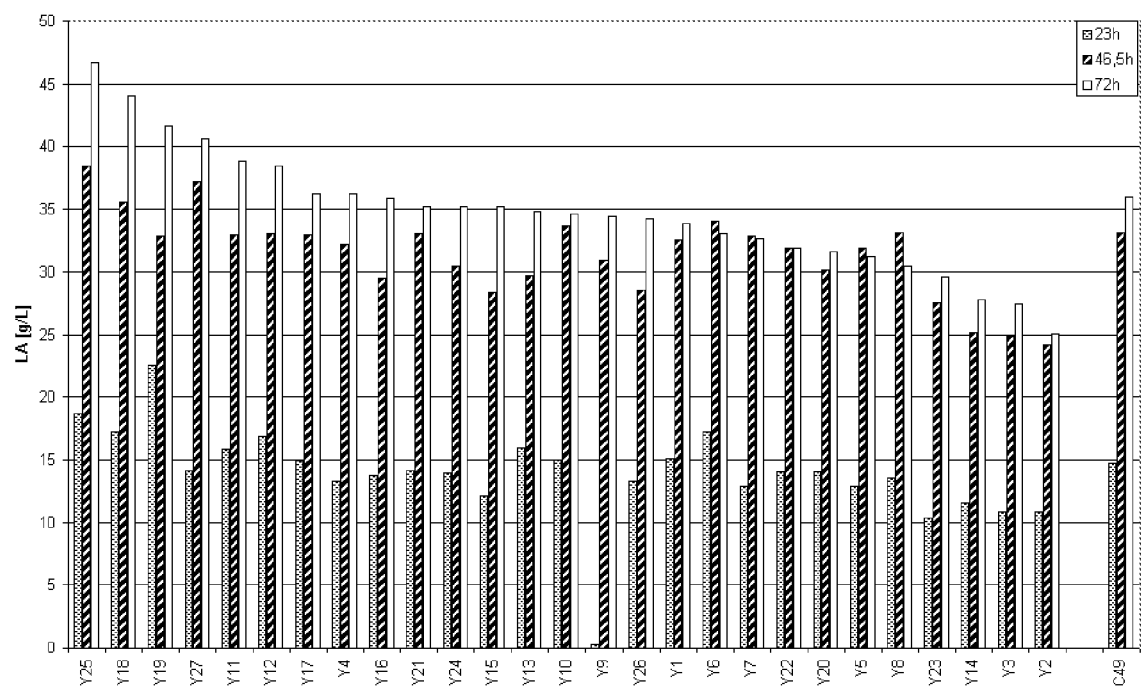
FIG. 8 shows a bar graph of the lactic acid produced (LA g/L) after 23, 46.5 and 70 hours of growth for 27 strains derived from mutagenesis of sorted (with 100 g/L glucose) C49 strain. The 27 strains are compared with the parental strain C49 (right side of the plot).
Figure 9:
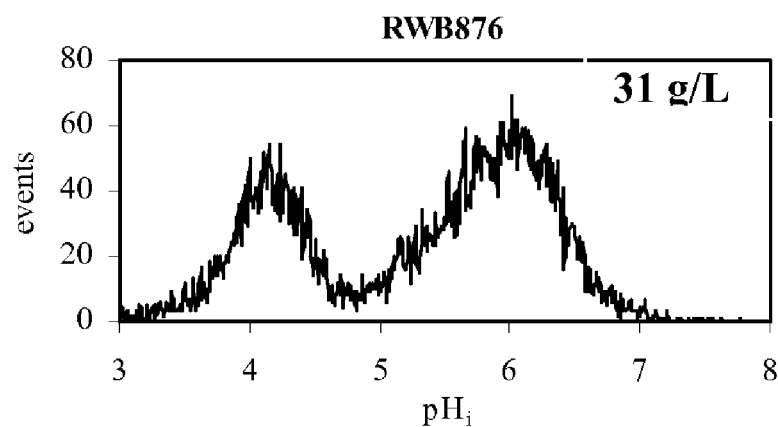
FIG. 9 shows histograms of the distribution of the $pH_i$ values in cell populations of the S. cerevisiae strains RWB876, G33 and m850 respectively, after 70 hours of growth. The lactic acid produced by the respective strains after 70 hours of growth is reported in the histograms.
Figure 9:
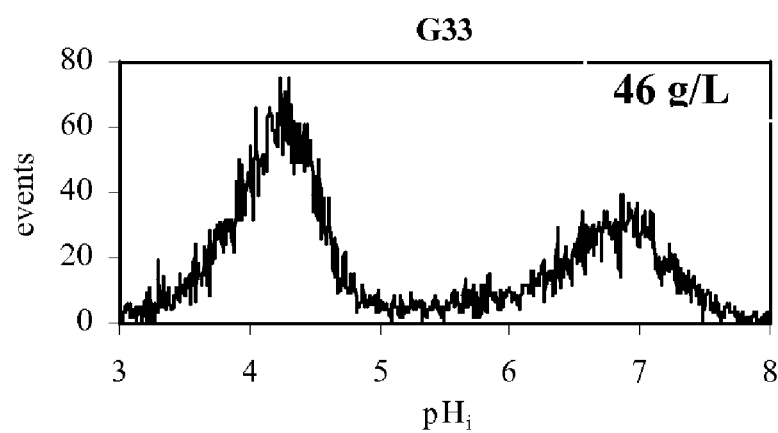
Figure 9:
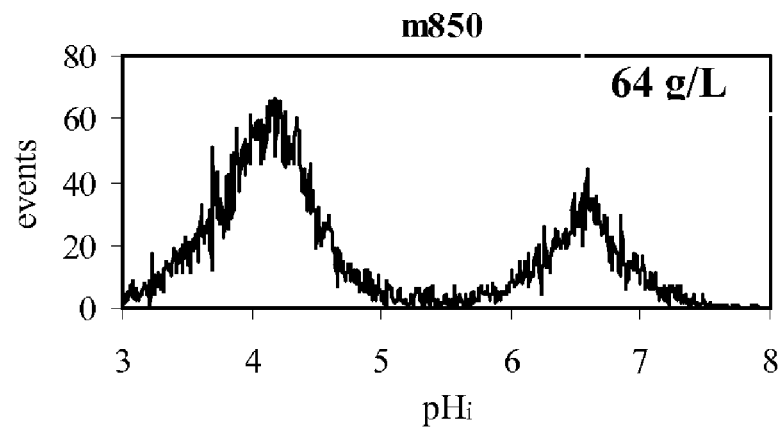

A total of 26 strains derived from mutagenesis of m850 and 27 strains derived from mutagenesis of C49 were tested in a lactic acid production assay, with results shown in FIGS. 7-8. FIG. 7 shows results of screening of 26 presumptive mutants isolated from the UV mutagenized and sorted (with 100 g/L glucose) m850 strain. In the plot the lactic acid produced (LA g/L) after 23, 46.5 and 70 hours of growth are reported. The 26 presumptive mutants are compared with the parental strain m850 (right side of the plot). FIG. 8 shows the results of screening of 27 presumptive mutants isolated from the UV mutagenized and sorted (with 100 g/L glucose) C49 strain. In the plot the lactic acid produced (LA g/L) after 23, 46.5 and 70 hours of growth are reported. The 27 presumptive mutants are compared with the parental strain C49 (right side of the plot).

EXAMPLE 5

*S. cerevisiae* strain m850 was subjected to mutagenesis as described in Example 2 and two mutant strains, labeled Z22 and Z26, were isolated from the yeast population as described in Example 4. Lactic acid synthesis by m850, Z22, and Z26 was measured in an aqueous medium containing 2.78 g/L CaCO$_3$, 75 g/L glucose, 1.7 g/L YNB, 1 g/L urea, and 5 ml/L ethanol.

10 ml of supernatant were collected at time points up to 70 hours after inoculation of the fermentation medium for all strains. The experiments were performed in duplicate (the notation "_bis" indicating the second run of each experiment). The optical density at 600 nm, the medium lactic acid concentration, the medium glucose concentration, and the external pH (pH$_e$) of each sample at the various time points are reported in Tables 5-1 to 5-4, below. Significant results are indicated in bold. n.d., not determined.

TABLE 5-1

| | OD$_{600}$ | | | | | |
|---|---|---|---|---|---|---|
| | hr after inoc. | | | | | |
| | 0 | 15 | 22 | 36 | 47.5 | 62 | 70 |
| m850 | 2.9 | 8.15 | 9.0 | 12.2 | 13.5 | 13.7 | 16.1 |
| Z22 | 2.9 | 8.55 | 10.8 | 14.4 | 15.5 | 17.3 | 18.8 |
| Z26 | 3.0 | 8.35 | 9.5 | 14.0 | 14.7 | 15.0 | 16.7 |
| m850_bis | 2.9 | 7.6 | 9.0 | 13.0 | 12.9 | 15.0 | 16.2 |
| Z22_bis | 3.1 | 8.9 | 11.1 | 14.2 | 15.5 | 18.0 | 18.3 |
| Z26_bis | 3.1 | 8.55 | 10.4 | 14.1 | 14.5 | 16.0 | 16.4 |

TABLE 5-2

| | Lactic acid (g/L) | | | | | |
|---|---|---|---|---|---|---|
| | hr after inoc. | | | | | |
| | 0 | 15 | 22 | 36 | 47 | 62 | 70 |
| m850 | n.d. | n.d. | 17.8 | 35.1 | 41.5 | 54.7 | 60.9 |
| Z22 | n.d. | n.d. | 18.3 | 35.1 | 44.5 | 59.7 | 63.5 |
| Z26 | n.d. | n.d. | 14.4 | 39.9 | 50.1 | 64.9 | 67.5 |
| m850_bis | n.d. | n.d. | 18.2 | 36.3 | 44.5 | 56.1 | 61.9 |
| Z22_bis | n.d. | n.d. | 18.3 | 35.9 | 43.4 | 61.3 | 66.5 |
| Z26_bis | n.d. | n.d. | 20.4 | 40.1 | 48.9 | 61.9 | 69.9 |

TABLE 5-3

| | Glucose, g/L | | | | | |
|---|---|---|---|---|---|---|
| | hr after inoc. | | | | | |
| | 0 | 15 | 22 | 36 | 47 | 62 | 70 |
| m850 | 74.8 | n.d. | 53.7 | 34.2 | 25.2 | 12.4 | 5.9 |
| Z22 | 76.9 | n.d. | 54.6 | 33.8 | 25.2 | 10.9 | 4.6 |
| Z26 | 75.5 | n.d. | 34.5 | 29.9 | 20.7 | 6.1 | 0.8 |
| m850_bis | 75.6 | n.d. | 57.6 | 36.7 | 26.5 | 12.1 | 5.5 |
| Z22_bis | 76.3 | n.d. | 61.1 | 35.1 | 24.5 | 10.7 | 4.5 |
| Z26_bis | 75.6 | n.d. | 51.6 | 31.6 | 20.8 | 6.2 | 0.8 |

TABLE 5-4

| | pH$_e$ | | | | | |
|---|---|---|---|---|---|---|
| | hr after inoc. | | | | | |
| | 0 | 15 | 22 | 36 | 47 | 62 | 70 |
| m850 | 6.1 | 3.6 | 3.2 | 2.8 | 2.57 | 2.47 | 2.42 |
| Z22 | 6.1 | 3.6 | 3.2 | 2.8 | 2.57 | 2.46 | 2.42 |
| Z26 | 6.1 | 3.5 | 3.1 | 2.7 | 2.52 | 2.42 | 2.37 |
| m850_bis | 6.1 | 3.62 | 3.1 | 2.8 | 2.57 | 2.46 | 2.4 |
| Z22_bis | 6.1 | 3.6 | 3.2 | 2.8 | 2.57 | 2.46 | 2.39 |
| Z26_bis | 6.1 | 3.5 | 3.1 | 2.7 | 2.52 | 2.42 | 2.37 |

Tables 5-1 to 5-4 indicate that under essentially the same pH$_e$ and cell density (OD$_{600}$), after 70 hr, mutant strain Z26 produced about 10% more lactic acid than m850 and consumed much more of the initial glucose charge than m850.

EXAMPLE 6

*S. cerevisiae* strains m850, Z22, and Z26, as described in Examples 4 and 5, were used, and a third mutant strain, Y27, was prepared in the same manner as Z22 and Z26, as described in Example 5. Lactic acid synthesis by m850, Z22, Z26, and Y27 was measured essentially as described in Example 5 in an aqueous medium containing 2.78 g/L CaCO$_3$, 80 or 90 g/L glucose, 1.7 g/L YNB, 1 g/L urea, 5 ml/L ethanol. The glucose concentration is given by the notation "_80 g/L" or "_90 g/L" in Tables 6-1 to 6-4, below.

10 ml of supernatant were collected at various time points up to 88.5 hours after inoculation for all strains. The optical density at 600 nm, the medium lactic acid concentration, the medium glucose concentration, and the external pH (pH$_e$) of each sample at the various time points are reported in Tables 6-1 to 6-4, below. Significant results are indicated in bold. n.d., not determine.

TABLE 6-1

OD$_{600}$

| | hr after inoc. | | | | | | | |
|---|---|---|---|---|---|---|---|---|
| | 0 | 14 | 22 | 36.5 | 46 | 63 | 70 | 88.5 |
| m850_80 g/L | 3.0 | 7.54 | 9.0 | 11.7 | 13.1 | 13.9 | 14.6 | 15.7 |
| Z22_80 g/L | 3.1 | 8.04 | 9.3 | 12.1 | 14.5 | 15.7 | 16.5 | 17.3 |
| Z26_80 g/L | 3.0 | 8.14 | 9.7 | 12.3 | 14.4 | 14.6 | 14.7 | 14.3 |
| Y27_80 g/L | 3.0 | 7.6 | 8.6 | 11.2 | 11.8 | 11.1 | 11.1 | 12 |
| m850_90 g/L | 3.0 | 7.58 | 8.6 | 10.7 | 12.8 | 14.1 | 14.7 | 15.1 |
| Z22_90 g/L | 2.9 | 8.02 | 10.1 | 12.8 | 14.6 | 15.0 | 15.9 | 16.55 |
| Z26_90 g/L | 3.1 | 7.68 | 9.7 | 12.3 | 13.4 | 13.1 | 14.0 | 13.85 |
| Y27_90 g/L | 3.0 | 7.26 | 8.5 | 11.4 | 13.2 | 11.4 | 11.0 | 11.5 |

TABLE 6-2

Lactic acid, g/L

| | hr after inoc. | | | | | | | |
|---|---|---|---|---|---|---|---|---|
| | 0 | 14 | 22 | 36.5 | 46 | 62 | 70 | 88.5 |
| m850_80 g/L | n.d. | n.d. | 18.9 | 35.8 | 48.1 | 61.9 | 66.7 | 71.5 |
| Z22_80 g/L | n.d. | n.d. | 18.5 | 35.4 | 48.1 | 63.9 | 71.1 | 76.7 |
| Z26_80 g/L | n.d. | n.d. | 22.0 | 39.7 | 48.7 | 71.7 | 77.3 | 75.1 |
| Y27_80 g/L | n.d. | n.d. | 20.1 | 31.2 | 46.1 | 57.1 | 59.7 | 57.3 |
| m850_90 g/L | n.d. | n.d. | 18.8 | 31.5 | 46.7 | 62.3 | 68.5 | 77.1 |
| Z22_90 g/L | n.d. | n.d. | 18.5 | 35.3 | 49.9 | 64.9 | 71.3 | 78.5 |
| Z26_90 g/L | n.d. | n.d. | 20.5 | 45.1 | 55.7 | 71.1 | 76.5 | 86.9 |
| Y27_90 g/L | n.d. | n.d. | 19.2 | 36.3 | 46.7 | 57.7 | 61.5 | 61.1 |

TABLE 6-3

Glucose, g/L

| | hr after inoc. | | | | | | | |
|---|---|---|---|---|---|---|---|---|
| | 0 | 14 | 22 | 36.5 | 46 | 62 | 70 | 88 |
| m850_80 g/L | 81.9 | n.d. | n.d. | n.d. | 30.2 | 13.5 | 8.2 | 0.0 |
| Z22_80 g/L | 81.1 | n.d. | n.d. | n.d. | 29.5 | 12.2 | 7.6 | 0.2 |
| Z26_80 g/L | 79.3 | n.d. | n.d. | n.d. | 29.7 | 4.6 | 0.3 | 0.0 |
| Y27_80 g/L | 80.8 | n.d. | n.d. | n.d. | 30.8 | 17.0 | 14.9 | 11.2 |
| m850_90 g/L | 89.1 | n.d. | n.d. | n.d. | 38.0 | 22.3 | 18.2 | 8.2 |
| Z22_90 g/L | 87.1 | n.d. | n.d. | n.d. | 37.3 | 23.8 | 18.6 | 9.3 |
| Z26_90 g/L | 89.8 | n.d. | n.d. | n.d. | 32.7 | 16.7 | 11.9 | 2.1 |
| Y27_90 g/L | 88.2 | n.d. | n.d. | n.d. | 39.8 | 27.7 | 24.7 | 19.3 |

TABLE 6-4 pH$_e$

| | hr after inoc. | | | | | | | |
|---|---|---|---|---|---|---|---|---|
| | 0 | 14 | 22 | 36.5 | 46 | 63 | 70 | 88.5 |
| m850_80 g/L | 6.15 | 3.7 | 3.18 | 2.78 | 2.67 | 2.54 | 2.49 | 2.44 |
| Z22_80 g/L | 6.2 | 3.6 | 3.15 | 2.76 | 2.64 | 2.52 | 2.45 | 2.43 |
| Z26_80 g/L | 6.2 | 3.54 | 3.06 | 2.7 | 2.64 | 2.47 | 2.4 | 2.44 |
| Y27_80 g/L | 6.2 | 3.54 | 3.1 | 2.77 | 2.64 | 2.54 | 2.48 | 2.48 |
| m850_90 g/L | 6.2 | 3.63 | 3.15 | 2.76 | 2.64 | 2.52 | 2.49 | 2.43 |
| Z22_90 g/L | 6.2 | 3.6 | 3.14 | 2.75 | 2.64 | 2.51 | 2.54 | 2.42 |
| Z26_90 g/L | 6.18 | 3.5 | 3.07 | 2.71 | 2.6 | 2.48 | 2.45 | 2.37 |
| Y27_90 g/L | 6.2 | 3.6 | 3.11 | 2.77 | 2.64 | 2.52 | 2.53 | 2.46 |

Tables 6-1 to 6-4 indicate that under essentially the same pH$_e$ and cell density (OD$_{600}$), mutant strain Z26 produced about 8-12% more lactic acid than m850 and, from about 60-80 hr, consumed at least as much or more of the initial glucose charge than m850.

EXAMPLE 7

*S. cerevisiae* strain G33 was isolated from the mutagenized yeast population as described in Example 2. Lactic acid synthesis and pH$_i$ of the strains G33, RWB876, and m850 were measured essentially as described in Examples 2-4 in an aqueous medium containing 4.5 g/L CaCO$_3$, 70 g/L glucose, 1.7 g/L YNB, 1 g/L urea, and 5 ml/L ethanol.

In FIG. 8, the distribution of the pH$_i$ and the lactic acid produced from the respective strains after 70 hours of growth are reported. In all the strains two subpopulations of cells with different pH$_i$ values are present. As described in example 1 the cells belonging to the subpopulation with low pH$_i$ (below pH$_i$ 5.0) are dead cells, while cells belonging to the subpopulation with the high pH$_i$ are viable. The figures show that the subpopulation of viable cells of the strain G33 have a higher pH$_i$ value than the parental strain RWB 876. Furthermore, the strain G33 produced about 50% more lactic acid than the parental strain RWB 876.

All of the methods disclosed and claimed herein can be made and executed without undue experimentation in light of the present disclosure. While the methods of this invention have been described in terms of particular embodiments, it will be apparent to those of skill in the art that variations may be applied to the methods and in the steps or in the sequence of steps thereof without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of selecting a yeast population for production of an organic acid, comprising:
   staining a yeast population with a stain capable of internal pH (pH$_i$)-dependent fluorescence, to yield a stained yeast population;
   determining a gate pH and a corresponding fluorescence parameter of the stained yeast population; and
   sorting the cells of the stained yeast population such that the cells having a pH$_i$ above the gate pH are retained and the cells having a pH$_i$ below the gate pH are discarded, to yield the yeast population for the production of the organic acid.

2. The method of claim 1, wherein the organic acid is lactic acid.

3. The method of claim 1, wherein the yeast population are *Saccharomyces cerevisiae*.

4. The method of claim 1, wherein the stain is semi-naphtharhodafluor-4F 5-(and-6)-carboxylic acid, acetoxymethyl ester, acetate.

5. The method of claim 1, further comprising gating of viable cells such that living cells are retained and dead cells are discarded, to yield the yeast population for the production of the organic acid.

6. The method of claim 1, wherein the sorting step is performed two, three, or four times.

7. The method of claim 5, wherein the sorting step is performed two, three, or four times.

8. A method of producing an organic acid, comprising:

staining a yeast population with a stain capable of internal pH ($pH_i$)-dependent fluorescence, to yield a stained yeast population;

determining a gate pH and a corresponding fluorescence parameter of the stained yeast population;

sorting the cells of the stained yeast population such that the cells having a $pH_i$ above the gate pH are retained and the cells having a $pH_i$ below the gate pH are discarded, to yield a yeast population for the production of the organic acid; and incubating the yeast population for the production of an organic acid in a medium containing an organic acid precursor, to produce the organic acid.

9. The method of claim 8, further comprising isolating individual cells of the yeast population, to yield individual yeast cells for the production of an organic acid; culturing an individual yeast cell, to yield a cloned yeast population for the production of an organic acid.

10. The method of claim 8, wherein the organic acid is lactic acid.

11. The method of claim 8, wherein the yeast population are *Saccharomyces cerevisiae*.

12. The method of claim 8, wherein the stain is semi-naphtharhodafluor-4F 5-(and-6)-carboxylic acid, acetoxymethyl ester, acetate.

13. The method of claim 8, further comprising gating of viable cells such that living cells are retained and dead cells are discarded, to yield the yeast population for the production of the organic acid.

14. The method of claim 8, wherein the sorting step is performed two, three, or four times.

15. The method of claim 13, wherein the sorting step is performed two, three, or four times.

* * * * *